US00PP18744P2

(12) United States Plant Patent
Brown

(10) Patent No.: US PP18,744 P2
(45) Date of Patent: Apr. 22, 2008

(54) ***DIASCIA* PLANT NAMED 'CODI101'**

(50) Latin Name: *Diascia×hybrida*
Varietal Denomination: CODI101

(75) Inventor: Graham Noel Brown, Pennant Hills (AU)

(73) Assignee: Nuflora International Pty. Ltd., Macquarie Fields, NSW (AU)

( * ) Notice: Subject to any disclaimer, the term of this patent is extended or adjusted under 35 U.S.C. 154(b) by 0 days.

(21) Appl. No.: 11/637,850

(22) Filed: Dec. 12, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Diascia* plant named 'CODI101', characterized by its compact, dense, upright and outwardly spreading plant habit; freely flowering habit; and blue violet-colored flowers.

1 Drawing Sheet

Botanical designation: *Diascia×hybrida.*
Cultivar denomination: 'CODI101'.

BACKGROUND OF THE INVENTION

The present invention relates to a new and distinct cultivar of *Diascia,* botanically known as *Diascia×hybrida,* and hereinafter referred to by the name 'CODI101'.

The new *Diascia* is a product of a planned breeding program conducted by the Inventor in Cobbitty, New South Wales, Australia The objective of the breeding program is to create new freely-flowering *Diascia* cultivars with uniform plant habit and attractive flower colors.

The new *Diascia* originated from a cross-pollination made by the Inventor in Cobbitty, New South Wales, Australia in September, 2001 of a proprietary selection of *Diascia×hybrida* identified as code number X99.46.1, not patented, as the female, or seed, parent with a proprietary selection of *Diascia×hybrida* identified as code number X99.46.4, not patented, as the male, or pollen, parent. The cultivar CODI101 was discovered and selected by the Inventor as a flowering plant within the progeny of the stated cross-pollination in a controlled environment in Cobbitty, New South Wales, Australia in October, 2002.

Asexual reproduction of the new *Diascia* by terminal cuttings in a controlled environment in Macquarie Fields, New South Wales, Australia since October, 2002, has shown that the unique features of this new *Diascia* are stable and reproduced true to type in successive generations.

SUMMARY OF THE INVENTION

The cultivar CODI101 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'CODI101'. These characteristics in combination distinguish 'CODI101' as a new and distinct cultivar of *Diascia:*

1. Compact, dense, upright and outwardly spreading plant habit.
2. Freely flowering habit.
3. Blue violet-colored flowers.

Plants of the new *Diascia* can be compared to plants of the female parent selection. Plants of the new *Diascia* differ from plants of the female parent selection primarily in flower size as plants of the new *Diascia* have larger flowers than plants of the female parent selection.

Plants of the new *Diascia* can be compared to plants of the male parent selection. Plants of the new *Diascia* differ primarily from plants of the male parent selection in flower color as plants of the new *Diascia* have more reddish-colored flowers.

Plants of the new *Diascia* can be compared to plants of the *Diascia×hybrida* cultivar Codiared, disclosed in U.S. Plant Pat. No. 13,176. In side-by-side comparisons conducted in Macquarie Fields, New South Wales, Australia, plants of the new *Diascia* differed primarily from plants of the cultivar Codiared in flower color as plants of the cultivar Codiared had red purple-colored flowers.

BRIEF DESCRIPTION OF THE PHOTOGRAPHS

The accompanying colored photographs illustrate the overall appearance of the new *Diascia,* showing the colors as true as it is reasonably possible to obtain in colored reproductions of this type. Colors in the photographs may differ slightly from the color values cited in the detailed botanical description which accurately describe the colors of the new *Diascia.*

The photograph at the bottom of the sheet comprises a side perspective view of a typical flowering plant of 'CODI101' grown in a container.

The photograph at the top of the sheet comprises a close-up view of typical flowers of 'CODI101'.

DETAILED BOTANICAL DESCRIPTION

The aforementioned photographs and following observations, measurements and values describe plants grown in Encinitas, Calif. in 12.5-cm containers in an outdoor nursery during the summer and under conditions which closely approximate commercial production. During the production of the plants, day temperatures averaged 24° C., night temperatures averaged 12° C. and light levels averaged 6,000 footcandles. Plants were pinched twice and were about 14 weeks old when the photographs and the description were taken. In the description, color references are made to The Royal Horticultural Society Colour Chart, 1995 Edition, except where general terms of ordinary dictionary significance are used.

Botanical classification: *Diascia×hybrida* cultivar CODI101.

Parentage:

*Female, or seed, parent.*—Proprietary selection of *Diascia×hybrida* identified as code number X99.46.1, not patented.

*Male or pollen parent.*—Proprietary selection of *Diascia×hybrida* identified as code number X99.46.4, not patented.

Propagation:

*Type.*—By terminal vegetative cuttings.

*Time to initiate roots, summer and winter.*—About one week at temperatures of 20° C.

*Time to develop roots, summer and winter.*—About three weeks at temperatures of 20° C.

*Root description.*—Fine, fibrous; white in color.

*Rooting habit.*—Freely branching; dense.

Plant description:

*Plant form and growth habit.*—Compact, dense, upright and outwardly spreading plant habit. Vigorous growth habit.

*Branching habit.*—Freely branching, usually about twelve primary lateral branches each with potentially two secondary lateral branches per node.

*Plant height.*—About 25 cm.

*Plant diameter* (*area of spread*).—About 38 cm.

Lateral branch description:

*Length.*—About 20 cm.

*Diameter.*—About 2 mm.

*Internode length.*—About 1.8 cm.

*Texture.*—Smooth, glabrous.

*Color.*—144A.

Foliage description:

*Arrangement.*—Opposite, simple.

*Length.*—About 3.5 cm.

*Width.*—About 2.8 cm.

*Shape.*—Elliptical with cordate tendencies.

*Apex.*—Broadly acute to rounded.

*Base.*—Cordate.

*Margin.*—Shallow and irregularly serrated.

*Texture, upper and lower surfaces.*—Smooth, glabrous.

*Venation pattern.*—Palmate; arcuate.

*Color.*—Developing and fully expanded foliage, upper surface: 147A; venation, 147C. Developing and fully expanded foliage, lower surface: 147B; venation, 147C.

*Petiole.*—Length: About 3 mm. Diameter: About 2.5 mm. Texture, upper and lower surfaces: Smooth, glabrous. Color, upper and lower surfaces: 147C.

Flower description:

*Flower arrangement.*—Single flowers arranged on loose terminal racemes. Freely flowering habit with usually about 65 open flowers and flower buds per lateral branch. Flowers face upright and outwardly. Flowers not fragrant.

*Natural flowering season.*—Plants flower continuously throughout the spring in southern California. Flowers last about five days on the plant. Flowers not persistent.

*Inflorescence height.*—About 11.5 cm.

*Inflorescence width.*—About 3.8 cm.

*Flower diameter.*—About 1.6 cm.

*Flower length* (*height*).—About 9 mm.

*Flower bud.*—Length: About 6 mm. Diameter: About 7 mm. Shape: Rounded. Color: 91C.

*Petals.*—Arrangement: Corolla consists of five petals modified into two banner petals, two lateral petals with spurs and a protruding lip petal. Length: Banner petals: About 4 mm. Lateral petals (including spurs): About 6 mm. Lower lip petal: About 1 cm. Width: Banner petals: About 4 mm. Lateral petals: About 5 mm. Lower lip petal: About 9 mm. Shape: Rounded. Apex: Rounded. Base: Attenuate. Margin: Entire; lower lip petal, slightly serrate. Texture, upper and lower surfaces: Smooth, glabrous, satiny. Color: When opening, upper surface: 94C. When opening, lower surface: 91C. Fully opened, upper surface: 90A to 90B; towards the base of lower lip petal, 87B; central eyespot, 12B. Fully opened, lower surface: Slightly more grey than 91B.

*Sepals.*—Appearance: Five sepals fused into a star-shaped calyx. Length: About 2.5 mm. Width: About 1 mm. Shape: Elliptical. Apex: Acute. Margin: Entire. Texture, upper surface: Smooth, glabrous. Texture, lower surface: Minute pubescence. Color, upper and lower surfaces: 144A.

*Peduncles.*—Length: About 3.5 cm. Diameter: About 1 mm. Angle: Erect to about 45° from vertical. Strength: Strong. Texture: Scattered pubescence. Color: 137A.

*Pedicels.*—Length: About 1.6 cm. Diameter: Less than 1 mm. Angle: About 45° from vertical. Strength: Moderately strong. Texture: Scattered pubescence. Color: 144A.

*Reproductive organs.*—Androecium: Stamen number: About four. Filament length: About 2 mm. Filament color: 71A. Anther shape: Ovoid. Anther length: Less than 1 mm. Anther color: 14A. Amount of pollen: Scarce. Pollen color: 14A. Gynoecium: Pistil length: About 4 mm. Style length: About 2 mm. Style color: 144B. Stigma appearance: Rounded. Stigma color: 144A. Ovary color: 146C.

*Seed/fruit.*—Seed and fruit production has not been observed.

Temperature tolerance: Plants of the new *Diascia* have been observed to tolerate temperatures from about 0° C. to about 32° C.

Pathogen/pest resistance: Plants of the new *Diascia* have not been shown to be resistant to pathogens and pests common to *Diascia*.

It is claimed:

1. A new and distinct *Diascia* plant named 'CODI101' as illustrated and described.

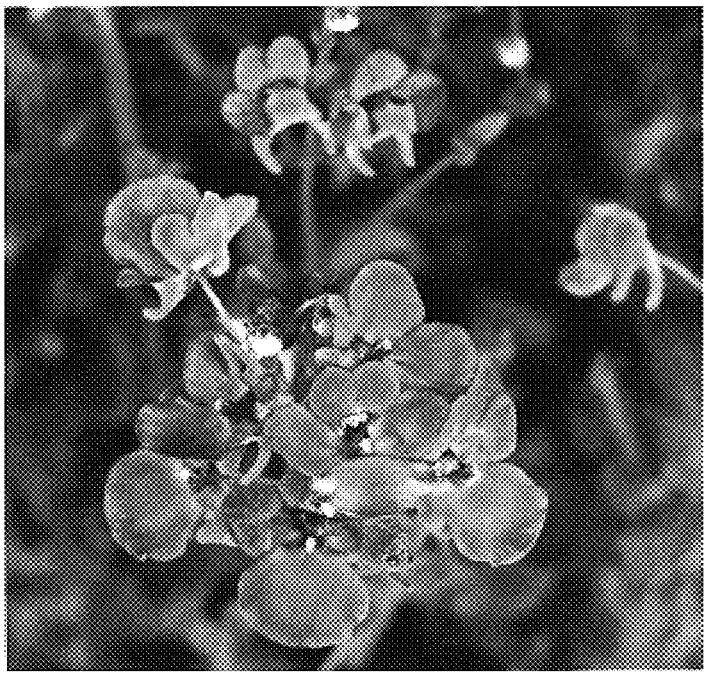
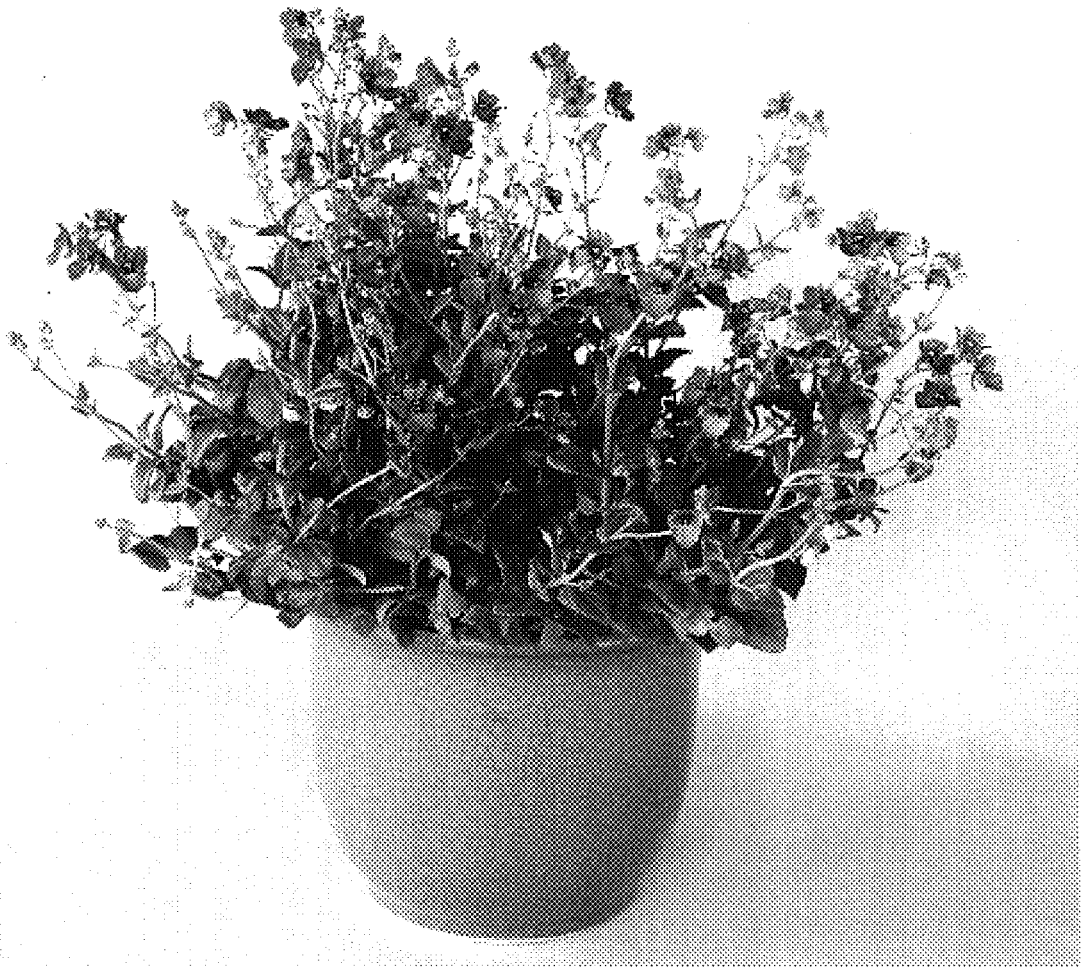

* * * * *